United States Patent [19]

Takahata et al.

[11] 4,198,535

[45] Apr. 15, 1980

[54] PROCESS FOR PRODUCING LINEAR UNSATURATED DIMERS OF α-ALKYL STYRENES

[75] Inventors: Kazunori Takahata, Ichihara; Hiroshi Hasui, Tokyo, both of Japan

[73] Assignee: Mitsui Petrochemical Industries Ltd., Tokyo, Japan

[21] Appl. No.: 946,301

[22] Filed: Sep. 27, 1978

[30] Foreign Application Priority Data

Sep. 27, 1977 [JP] Japan .................................. 52/115086

[51] Int. Cl.² ............................................. C07C 15/14
[52] U.S. Cl. .................................. 585/406; 252/52 R;
 252/73; 585/400; 585/404; 585/410; 585/415;
 585/476
[58] Field of Search ............... 260/669, 668 R, 668 F;
 252/52 R, 73

[56] References Cited

U.S. PATENT DOCUMENTS 3,925,217  12/1975  Green ................................. 252/52 R

FOREIGN PATENT DOCUMENTS 41-633566  4/1966  Japan .

Primary Examiner—Veronica O'Keefe
Attorney, Agent, or Firm—Sughrue, Rothwell, Mion, Zinn and Macpeak

[57] ABSTRACT

A process for producing a linear unsaturated dimer of α-alkyl styrenes by heating α-alkyl styrenes in the presence of a silica-alumina catalyst, said catalyst consisting of alumina and silica in a weight ratio of $83/17 \leq Al_2O_3/SiO_2 \leq 96/4$ and being substantially free of alkali is disclosed.

12 Claims, No Drawings

PROCESS FOR PRODUCING LINEAR UNSATURATED DIMERS OF α-ALKYL STYRENES

BACKGROUND OF THE INVENTION

1. Field of the Invention

This invention relates to a process for selectively producing a linear dimer of α-alkyl styrenes in high yield by dimerizing or codimerizing α-alkyl styrenes.

2. Description of the Prior Art

It is known that dimerization or codimerization of α-alkyl styrenes (herein dimerization and codimerization are simply referred to as dimerization, unless otherwise stated) produces one cyclic saturated dimer and two linear unsaturated dimers. For instance, dimerization of α-methyl styrene produces the cyclic dimer, 1,1,3-trimethyl-3-phenylindane, the two linear unsaturated dimers, 2,4-diphenyl-4-methyl-1-pentene and 2,4-diphenyl-4-methyl-2-pentene.

Heretofore, such linear unsaturated dimers have been produced, for example, using an aromatic or aliphatic sulfonic acid or solid acid, e.g., silica gel or silica-alumina, as a catalyst (Japanese Pat. No. 6335/66), by adding a divalent or polyvalent alcohol to a reaction system containing a solid acid or cation exchange resin (Japanese Pat. No. 32845/74), or by adding a monovalent alcohol to a reaction system containing a solid acid or cation exchange resin (Japanese patent application (OPI) No. 76051/75) (The term "OPI" as used herein refers to a "published unexamined Japanese patent application"). U.S. Pat. No. 3,925,217 to Green et al also discloses preparing unsaturated α-alkyl styrene dimers by contacting the monomer with a catalyst material, such as a mixture of phosphorous oxyhalide and a small amount of a strong mineral acid. Also, disclosed therein as catalysts are acidic clays, such as activated montmorillonite and Lewis acid catalysts. These processes, however, involve many disadvantages.

The method described in Japanese Pat. No. 6335/66 which relies on the sulfonic acid catalyst requires a special reactor that prevents acid corrosion, and, in addition, if the reaction temperature is elevated to increase the dimerization rate, selectivity for the linear unsaturated dimer sharply decreases. When the catalyst, silica gel or a silica-alumina, containing 15% alumina, the method has two major defects. One defect is that the activity of the catalyst is so low that dimerization does not proceed unless the solid acid is used in an amount as high as 50 to 200% by weight based on the weight of the α-alkyl styrenes. The other is that elevation of the reaction temperature to increase the dimerization rate results in a significant drop in the selectivity for the linear unsaturated dimer.

The method described in Japanese Pat. No. 32845/74 has eliminated these defects but is complicated by the addition of water and divalent or polyvalent alcohols. The same problem is true for the method described in Japanese patent application (OPI) No. 76051/75 that adds a monovalent alcohol to the reaction system. This method also suffers from the defect that the reaction cannot be stabilized at temperatures higher than 100° C. due to the high dimerization rate, consequently, the reaction must be carried out at low temperatures that slow down the dimerization rate significantly.

U.S. Pat. No. 3,994,816 describes a method of preparing a substantially hydrogenated linear dimer from α-methyl styrene, however, in this reaction, the α-methyl styrene is charged to an autoclave and the catalyst is Raney nickel.

Japanese Pat. No. 6335/66 discloses an example wherein an unsaturated dimer is selectively synthesized in the presence of a silica-alumina catalyst. The details of the catalyst composition are not disclosed except that the alumina content of the catalyst is 15 wt%. As a result of the various studies which have been conducted in attempting to achieve the above purposes of this invention, the present inventors have found that dimerization in the presence of a solid acid catalyst containing alumina and silica in a weight ratio of alumina to silica of 15/85 and which is substantially free of alkali produces a cyclic saturated dimer without the formation of linear unsaturated dimers. The present inventors have also found that if an alumina-silica catalyst that is substantially free of alkali is used, having an alumina to silica weight ratio of from 83/17 to 96/4 provides a high conversion of α-alkyl styrenes to dimers, high selectivity for the linear unsaturated dimer, and retains such high selectivity satisfactorily at temperatures higher than 120° C.

Some of the so-called "silica-alumina" catalysts contain oxides of an alkaline metal or an alkaline earth metal such as sodium oxide, calcium oxide and magnesium oxide. These oxides affect the catalytic action of the solid acid catalyst and especially affect the dimerization rate. The dimerization rate sharply decreases if a silica-alumina catalyst having a weight ratio of $Al_2O_3$ to $SiO_2$ from 83/17 to 96/4 inclusive contains more than $2.0 \times 10^{-4}$ mol/g of such oxides. Accordingly, the amount of these alkaline and alkaline earth metal oxides in the silica-alumina catalyst of the present invention must be less than $2.0 \times 10^{-4}$ mol/g, and is preferably less than $0.2 \times 10^{-4}$ mol/g, and most preferably less than $0.05 \times 10^{-4}$ mol/g.

SUMMARY OF THE INVENTION

It is, therefore, the object of this invention to eliminate the drawbacks in the conventional methods discussed above by providing a catalyst that does not complicate the reaction system and which is required in only small amounts to produce selectively a linear unsaturated dimer of α-alkyl styrenes in high yields and a catalyst which retains a high selectivity for the unsaturated dimer at high temperatures that provide a higher dimerization rate.

In summary, this invention relates to a process for producing the linear unsaturated dimer of α-alkyl styrenes by heating the α-alkyl styrenes in the presence of a silica-alumina catalyst, said catalyst consisting of alumina and silica in a weight ratio of from 83/17 to 96/4 and being substantially free of alkali.

The unsaturated dimers which are produced in accordance with the present invention are particularly suitable as lubricants for roller bearings (See U.S. Pat. No. 3,925,217) and as power transmission fluids (See U.S. Pat. No. 3,994,816).

DETAILED DESCRIPTION OF THE INVENTION

The proportion by weight of alumina to silica that constitutes the silica-alumina catalyst used in this invention must be in the range from 83/17 to 96/4. Using more alumina is industrially useless because dimerization of α-alkyl styrenes hardly occurs. If the amount of alumina is less than its lower limit or the amount of silica is larger than its upper limit, dimerization is promoted, but then the proportion of the unsaturated dimer produced increases and thereby the selectivity of the catalyst for the linear unsaturated dimer is significantly reduced. A preferred range of alumina to silica is from 85/15 to 93/7 based on weight.

The silica-alumina catalyst characterized by the alumina to silica weight ratio of from 83/17 to 96/4 can be easily prepared by known methods. For instance, hydrogels of alumina and silica that have been separately synthesized may be intimately mixed in suitable proportion, followed by drying and calcination of the mixture. For example, the catalyst can be produced by adding aqueous ammonia to an aqueous solution comprising a soluble salt containing Al, such as aluminum sulfate, aluminum chloride and aluminum nitrate, and a soluble salt containing Si, such as sodium metasilicate ($Na_2SiO_3$), sodium 2-silicate ($Na_2Si_2O_5$), and water glass, to precipitate a mixture of hydrogels of alumina and silica; filtering the solution obtained and washing the product followed by drying. It is important to thoroughly wash the hydrogels obtained on precipitation to reduce the alkali and alkaline earth metals to the levels discussed above. After drying, the product is molded in the form of a powder, tablet or globule and heated at 200° to 600° C. for 3 to 10 hours, preferably 300° to 550° C. for 3 to 5 hours, to obtain the desired catalyst.

The catalyst can also be prepared by mixing a hydrogel of alumina ($Al(OH)_3$ and $H_2O$) and a hydrogel of silica ($Si(OH)_4$ and water), drying the mixture and molding the mixture in the form of a powder, tablet or globule, followed by heating the molding at 200° to 600° C. for 3 to 10 hours, preferably 300° to 550° C. for 3 to 5 hours. In this case, the starting hydrogels should be substantially free of alkali.

A commercial product having the trade name "Neobeat D" (manufactured by Mizusawa Kagaku) having an alumina to silica ratio of $Al_2O_3/SiO_2 = 90/10$ may also be used.

There is no particular limit on the amount of the silica-alumina catalyst that can be used in dimerization in this invention, but normally the catalyst is used in an amount of 1 to 50% by weight, preferably 2 to 30% by weight, based on α-alkyl styrenes.

The reaction temperature according to this invention is normally from about 50° to about 200° C., and preferably from about 80° to about 160° C. Relatively high temperatures are advantageously used to increase the dimerization rate.

The dimerization may be performed at either atmospheric pressure or up to 10 kg/cm² pressure.

A solvent is not particularly necessary in the process of this invention, but a nonpolar solvent, such as hydrocarbon solvent, may be employed. Suitable examples are aliphatic hydrocarbons, such as hexane, heptane, octane and the like; alicyclic hydrocarbons, such as cyclohexane, cyclopentane, dekalin and the like; aromatic hydrocarbons, such as benzene, toluene, xylene, ethylbenzene, cumene and the like.

Any α-alkyl styrene of the formula:

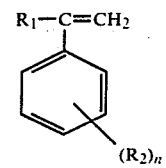

wherein $R_1$ is a lower alkyl group having 1 to 3 carbon atoms, such as methyl, ethyl, propyl or isopropyl group, preferably an alkyl group having 1 to 3 carbon atoms, more preferably methyl group; $R_2$ is a hydrogen atom or a lower alkyl group having 1 to 4 carbon atoms; and n is 1 to 5; may be used in this invention. Industrially advantageous to dimerize α-alkyl styrenes are α-methyl styrene, m- or p-methyl-α-methyl styrene, m- or p-ethyl-α-methyl styrene, m- or p-isopropyl-α-methyl styrene, α-ethyl styrene, m- or p-methyl-α-ethyl styrene, and m- or p-isobutyl-α-ethyl styrene. Particularly preferred are α-methyl styrene, α-ethyl styrene, m- or p-methyl-α-methyl styrene, and m- or p-isopropyl-α-methyl styrene. The unsaturated dimers produced in accordance with this invention are particularly suitable as lubricants as disclosed in U.S. Pat. No. 3,925,217. For this purpose, the dimer prepared from α-methyl styrene is particularly suitable.

According to the process of this invention, one α-alkyl styrene may be dimerized or two or more α-alkyl styrenes may be subjected to dimerization. In the latter case, the reaction is referred to herein as a "codimerization".

An industrial application of the process of this invention may be batchwise or continuously using a fixed bed.

The batchwise process is carried out at temperatures of 50° to 200° C., preferably 80° to 160° C., and even more preferably 120° to 150° C. The process is carried out under atmospheric to 10 kg/cm² pressure, although since the reaction occurs in the liquid phase high pressures are generally unnecessary. In the batch process, the catalyst may be in the form of a powder, tablet or globule. The amount of catalyst is 1 to 50% by weight based on the weight of the α-alkyl styrene, more preferably 2 to 30%. The batch reaction time is about 0.3 to 5 hours and more generally about 0.5 to 2 hours.

The continuous process is carried out by flowing the α-alkyl styrene over a fixed catalyst bed. The pressure and temperature conditions are the same as for the batch process. The α-alkyl styrene is fed through the bed such that the space velocity ($SV = F$ (l/hr)/V (l), where F is the α-alkyl styrene flow and V is the volume of the catalyst phase) is 0.05 $hr^{-1}$ to 5 $hr^{-1}$, and preferably 0.1 to 1 $hr^{-1}$. The density of the catalyst is 0.5 kg/l to 1.5 kg/l, preferably 0.7 to 1.2 kg/l. In the continuous process, the catalyst is preferably in the form of a globule or tablet.

The silica-alumina catalyst to be used in this invention may be in the form of a powder, tablet or globular. The globular and tablet form are preferred and are particularly preferred for the continuous process. The powder has a particle size of about 0.01 to 3 mm, the globule has a drop size of about 3 to 20 mm, the tablet diameter is about 3 to 20 mm and tablet thickness is 1 to 20 mm.

The unsaturated dimer may be isolated from the reaction product by conventional vacuum distillation.

The present invention enables the production of linear unsaturated dimers of α-alkyl styrenes in a simple reaction system with high selectivity and yield. Particularly advantageous is that a high yield of linear unsaturated dimer can be obtained at a temperature higher than 120° C. where dimerization proceeds at an increased rate. In addition, only a relatively small amount of the silica-alumina catalyst is necessary to produce the unsaturated dimer in accordance with the present invention.

The process of the present invention is now described in greater detail by reference to the following examples.

EXAMPLE 1

Preparation of Catalyst 9.7 g of colloidal silica "Snowtex O" (a product of Nissan Kagaku, containing 18.5 wt% of silica calculated from the amount of Si) and 182 g of alumina sol "Aluminazol-100" (a product of Nissan Kagaku, containing 10 wt% of alumina calculated from the amount of Al) were mixed together at 100° C. for 2 hours, dried at 500° C. for 3 hours, and ground to obtain 20 g of a powdered silica-alumina catalyst (particle size: 0.1 to 1 mm). The proportion of silica to alumina and the amount of sodium oxide contained in the catalyst are shown in the table below.

Dimerization

A 300 ml glass flask equipped with a stirrer and condenser was charged with 10 g of the catalyst and 100 g of α-methyl styrene and subjected to dimerization under stirring at 140° C. for 1 hour. After completion of the reaction, the resulting liquor was subjected to gas chromatography to determine its composition, the degree of conversion of α-methyl styrene, and the selectivity for the linear unsaturated dimer. The results are shown in the table below.

EXAMPLES 2 TO 5

Silica-alumina catalysts were prepared as in Example 1 except that the mixing ratio of colloidal silica to alumina sol was adjusted to provide the alumina to silica ratios indicated in the table below. Using these catalysts, dimerization was carried out under the same conditions as in Example 1. The composition of the resulting liquor, conversion of α-methyl styrene to dimers, and the selectivity for the linear unsaturated dimer are also set forth in the table below.

EXAMPLE 6

The procedure of Example 1 was repeated except that the commercial silica-alumina "Neobeat D" (particle size: 0.1 to 1 mm, a product of Mizusawa Kagaku) dried at 200° C. for 3 hours was used as the catalyst. The dimerization temperature was 150° C., and dimerization was carried out for 40 minutes. The composition of the dried Neobeat D, that of the resulting liquor, the degree of converting α-methyl styrene and the selectivity for the linear unsaturated dimer obtained are indicated in the table below.

EXAMPLE 7

The procedure of Example 1 was repeated except that 20 g of the catalyst prepared in Example 6 was used. The dimerization temperature was 100° C. and the dimerization time was 2 hours. The composition of the resulting liquor, the degree of conversion of α-methyl styrene, and the selectivity for the linear unsaturated dimer obtained are set forth in the table below.

EXAMPLE 8

A pyrex glass reaction tube having an inner diameter of 30 mm was filled with 50 ml of Neobeat D (50.2 g) (comprising 2–3 mm particles). The temperature of the catalytic bed was elevated to 150° C. while α-methyl styrene was supplied overhead at a rate of 50 ml/hr, space velocity 1.0 $hr^{-1}$. After the predetermined temperature was reached, the dimerization product was subjected to an analysis, which gave the degree of conversion of α-methyl styrene at 81%, selectivity for the linear unsaturated dimer at 94.1%, and the selectivity for the cyclic saturated dimer at 1.5%. No drop in the catalytic activity was observed even after 50 hours dimerization.

COMPARATIVE EXAMPLES 1 TO 4

Alumina-silica catalysts were prepared by repeating the procedure in Example 1 except that the mixing ratio of colloidal silica to alumina was changed to provide the catalysts shown in the Table. Using these catalysts, dimerization was performed according to the same method as employed in Example 1. The composition of the resulting layer, the degree of conversion of α-methyl styrene, and the selectivity for the linear unsaturated dimer are set forth in the Table. In Comparative Example 4 ($Al_2O_3/SiO_2 = 15/85$), dimerization was performed at 80° C. for 1 hour.

COMPARATIVE EXAMPLE 5

The procedure of Example 1 for preparing a catalyst and dimerization was repeated except that 0.48 g of sodium hydroxide per 100 ml water was added to the alumina and silica gel to prepare the catalyst. The composition of the resulting liquor, degree of conversion of α-methyl styrene, the selectivity for the linear unsaturated dimer obtained, and the composition of the catalyst are shown in the Table.

TABLE

|  |  | Silica-Alumina* | | Resulting Liquor | | | | Selectivity |
|---|---|---|---|---|---|---|---|---|
|  |  | Alumina/ Silica | Sodium Oxide (mol/g) | α-MS | Linear Unsaturated Dimer | Cyclic Saturated Dimer | Conversion (%) | of Linear Unsaturated Dimer |
| Example | 1 | 91/9 | $3 \times 10^{-6}$ | 18.8 | 77.8 | 2.3 | 81.2 | 95.8 |
|  | 2 | 96/4 | $1 \times 10^{-6}$ | 49.8 | 48.4 | 0.5 | 50.2 | 96.5 |
|  | 3 | 93/7 | $2 \times 10^{-6}$ | 33.0 | 63.8 | 1.4 | 67.0 | 95.2 |
|  | 4 | 85/15 | $5 \times 10^{-6}$ | 7.8 | 81.7 | 8.5 | 92.2 | 88.6 |
|  | 5 | 83/17 | $5 \times 10^{-6}$ | 7.0 | 81.2 | 10.2 | 93.0 | 87.3 |
|  | 6 | 90/10 | 0 | 15.0 | 80.6 | 2.0 | 85.0 | 94.8 |
|  | 7 | 90/10 | 0 | 36.5 | 59.3 | 1.0 | 63.5 | 93.4 |
| Comparative Example | 1 | 100/0 | 0 | 91.7 | 7.4 | 0.0 | 8.3 | 89.2 |
|  | 2 | 97/3 | $1 \times 10^{-6}$ | 90.1 | 8.9 | 0.0 | 9.9 | 89.9 |
|  | 3 | 80/20 | $6 \times 10^{-6}$ | 4.3 | 77.8 | 16.0 | 95.7 | 81.3 |

TABLE-continued

| | Silica-Alumina* | | Resulting Liquor | | | Conversion (%) | Selectivity of Linear Unsaturated Dimer |
|---|---|---|---|---|---|---|---|
| | Alumina/ Silica | Sodium Oxide (mol/g) | α-MS | Linear Unsaturated Dimer | Cyclic Saturated Dimer | | |
| 4 | 15/85 | $2.7 \times 10^{-5}$ | 0.0 | 0.0 | 98.1 | 100 | 0.0 |
| 5 | 91/9 | $3 \times 10^{-4}$ | 98.2 | 1.7 | 0.0 | 1.8 | 94.4 |

*The amount of magnesium or calcium oxide contained therein is $0.05 \times 10^{-4}$ mol or less.

While the invention has been described in detail and with reference to specific embodiments thereof, it will be apparent to one skilled in the art that various changes and modifications can be made therein without departing from the spirit and scope thereof.

What is claimed is:

1. A process for producing a linear unsaturated dimer of α-alkyl styrene which comprises heating at atmospheric pressure to 10 kg/cm²g an α-alkyl styrene in contact with a silica-alumina catalyst, said catalyst consisting essentially of alumina and silica in a weight ratio of alumina to silica of from 83/17 to 96/4 and said catalyst being substantially free of alkali.

2. The process according to claim 1, wherein said α-alkyl styrene is heated to a temperature of from about 50° to about 200° C.

3. The process according to claim 1, wherein the α-alkyl styrene is α-methyl styrene, α-ethyl styrene, m- or p-methyl-α-methyl styrene or m- or p-isopropyl-α-methyl styrene.

4. The process according to claim 1, wherein said process is a continuous or batch process.

5. The process according to claim 1, wherein said catalyst is in the form of a powder, tablet or globule.

6. The process according to claim 5, wherein said powder has a particle size of 0.01 to 3 mm, said globule has a drop size of 3 to 20 mm and said tablet has a diameter of 3 to 20 mm and a thickness of 1 to 20 mm.

7. The process according to claim 4, wherein said process is continuously performed over a fixed catalyst, said catalyst bed is maintained at a temperature of about 50° to 200° C. and said α-styrenes are fed to said bed at a space velocity of 0.05 to 5 hr$^{-1}$.

8. The process according to claim 4, wherein said process is a batch process, said catalyst is in the form of globule, tablet or powder and said process is carried out at about 50° to 200° C. under atmospheric pressure to 10 kg/cm².

9. The process according to claim 1, wherein two or more α-alkyl styrenes are dimerized.

10. The process according to claim 1, wherein said alumina for silica ratio is 85/15 to 93/7 based on weight.

11. The process according to claim 1, wherein said process is continuous and said catalyst has a density of 0.5 kg/l to 1.5 kg/l.

12. The process according to claim 1, wherein said process is conducted in the presence of less than $2.0 \times 10^{-4}$ mol/g of alkali.

* * * * *